US009993239B2

(12) United States Patent
Karpowicz et al.

(10) Patent No.: US 9,993,239 B2
(45) Date of Patent: Jun. 12, 2018

(54) SURGICAL RETRACTOR SYSTEM

(71) Applicant: GLOBUS MEDICAL, INC., Audubon, PA (US)

(72) Inventors: Edward Karpowicz, Sewell, NJ (US); Andrew Iott, Newtown Square, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days. days.

(21) Appl. No.: 15/483,489

(22) Filed: Apr. 10, 2017

(65) Prior Publication Data

US 2017/0273679 A1 Sep. 28, 2017

Related U.S. Application Data

(63) Continuation of application No. 14/630,085, filed on Feb. 24, 2015, now Pat. No. 9,649,101, which is a continuation of application No. 13/070,033, filed on Mar. 23, 2011, now Pat. No. 8,992,425, which is a continuation of application No. 11/422,511, filed on Jun. 6, 2006, now Pat. No. 7,935,053.

(51) Int. Cl.
*A61B 17/02* (2006.01)
*A61B 1/00* (2006.01)
*A61B 1/32* (2006.01)
*A61B 17/00* (2006.01)

(52) U.S. Cl.
CPC ...... *A61B 17/0293* (2013.01); *A61B 1/00135* (2013.01); *A61B 1/32* (2013.01); *A61B 17/025* (2013.01); *A61B 17/0206* (2013.01); *A61B 17/0218* (2013.01); *A61B 2017/00473* (2013.01); *A61B 2017/0256* (2013.01)

(58) Field of Classification Search
CPC ............ A61B 17/0206; A61B 17/0293; A61B 17/025
USPC ........................................................ 600/231
See application file for complete search history.

(56) References Cited

U.S. PATENT DOCUMENTS

| | | | |
|---|---|---|---|
| 5,688,223 A * | 11/1997 | Rosendahl | A61B 17/0293 600/201 |
| 5,944,736 A | 8/1999 | Taylor et al. | |
| 6,042,542 A | 3/2000 | Koros et al. | |
| 6,224,545 B1 * | 5/2001 | Cocchia | A61B 1/32 600/233 |
| 6,368,271 B1 | 4/2002 | Sharratt | |
| 6,416,467 B1 | 7/2002 | McMillan et al. | |
| 6,464,634 B1 | 10/2002 | Fraser | |
| 6,530,883 B2 | 3/2003 | Bookwalter et al. | |
| 6,712,795 B1 * | 3/2004 | Cohen | A61B 17/0206 604/233 |
| 6,723,044 B2 | 4/2004 | Pulford et al. | |
| 6,849,064 B2 | 2/2005 | Hamada | |

(Continued)

FOREIGN PATENT DOCUMENTS

EP 0455282 A2 3/1991

*Primary Examiner* — David Bates

(57) ABSTRACT

A surgical retractor system having a frame and a plurality of arms connected thereto is disclosed. At least one arm is moveable relative to the frame and the relative movement is constrained to a direction along the longitudinal axis of the arm. At least one retractor blade is removably connected to each of the plurality of arms. The blade is fixably rotatable about an axis normal to the longitudinal axis of the arm to which it is connected.

17 Claims, 17 Drawing Sheets

(56) References Cited

U.S. PATENT DOCUMENTS

| | | |
|---|---|---|
| 6,889,398 B2 | 3/2005 | Obenchain et al. |
| 6,874,392 B1 | 4/2005 | Wu |
| 7,014,608 B2 | 3/2006 | Larson |
| 7,137,949 B2 | 11/2006 | Scirica et al. |
| 7,195,592 B2 | 3/2007 | Ravikumar et al. |
| 7,922,658 B2 * | 4/2011 | Cohen .................... A61B 17/02 600/210 |
| 7,981,031 B2 * | 7/2011 | Frasier ................... A61B 17/02 600/224 |
| 8,100,828 B2 * | 1/2012 | Frey .................... A61B 17/0293 600/234 |
| 8,357,184 B2 * | 1/2013 | Woolley ............. A61B 17/0206 600/210 |
| 9,307,972 B2 * | 4/2016 | Lovell ................ A61B 17/0206 |
| 9,386,916 B2 * | 7/2016 | Predick .................... A61B 1/32 |
| 2004/0176665 A1 | 9/2004 | Branch et al. |
| 2005/0137461 A1 | 6/2005 | Marchek |
| 2005/0159651 A1 | 7/2005 | Raymond |
| 2005/0192485 A1 | 9/2005 | Branch et al. |
| 2005/0215866 A1 * | 9/2005 | Kim ................... A61B 17/0293 600/233 |
| 2005/0277812 A1 | 12/2005 | Gunter |
| 2006/0030858 A1 | 2/2006 | Simonson |
| 2007/0038033 A1 | 2/2007 | Jones et al. |
| 2007/0203399 A1 | 8/2007 | Gephart et al. |
| 2007/0208228 A1 * | 9/2007 | Pavento ............. A61B 17/0293 600/233 |
| 2008/0114209 A1 * | 5/2008 | Cohen ................ A61B 17/0206 600/210 |
| 2010/0217089 A1 * | 8/2010 | Farley .................... A61B 17/02 600/213 |

* cited by examiner

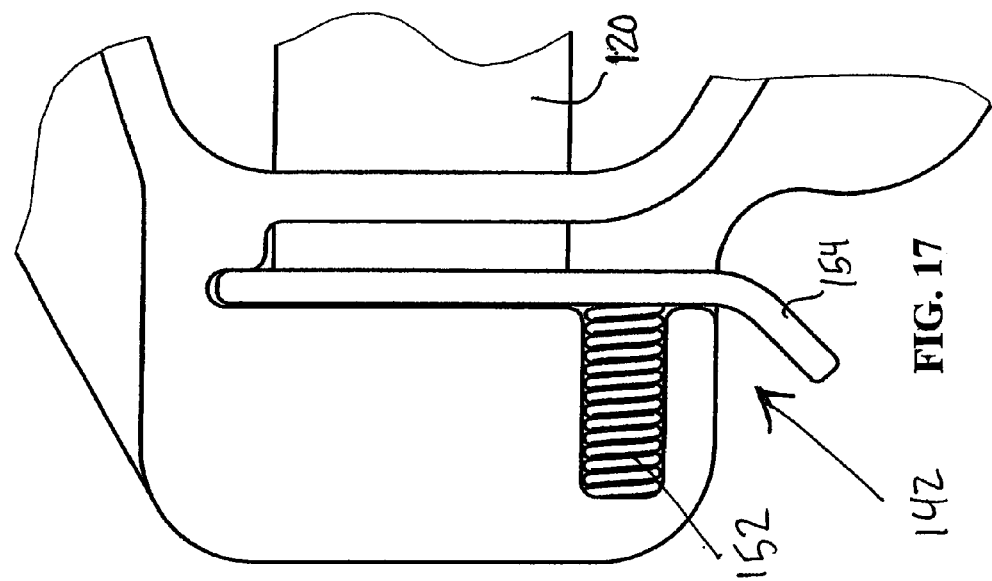
FIG. 17
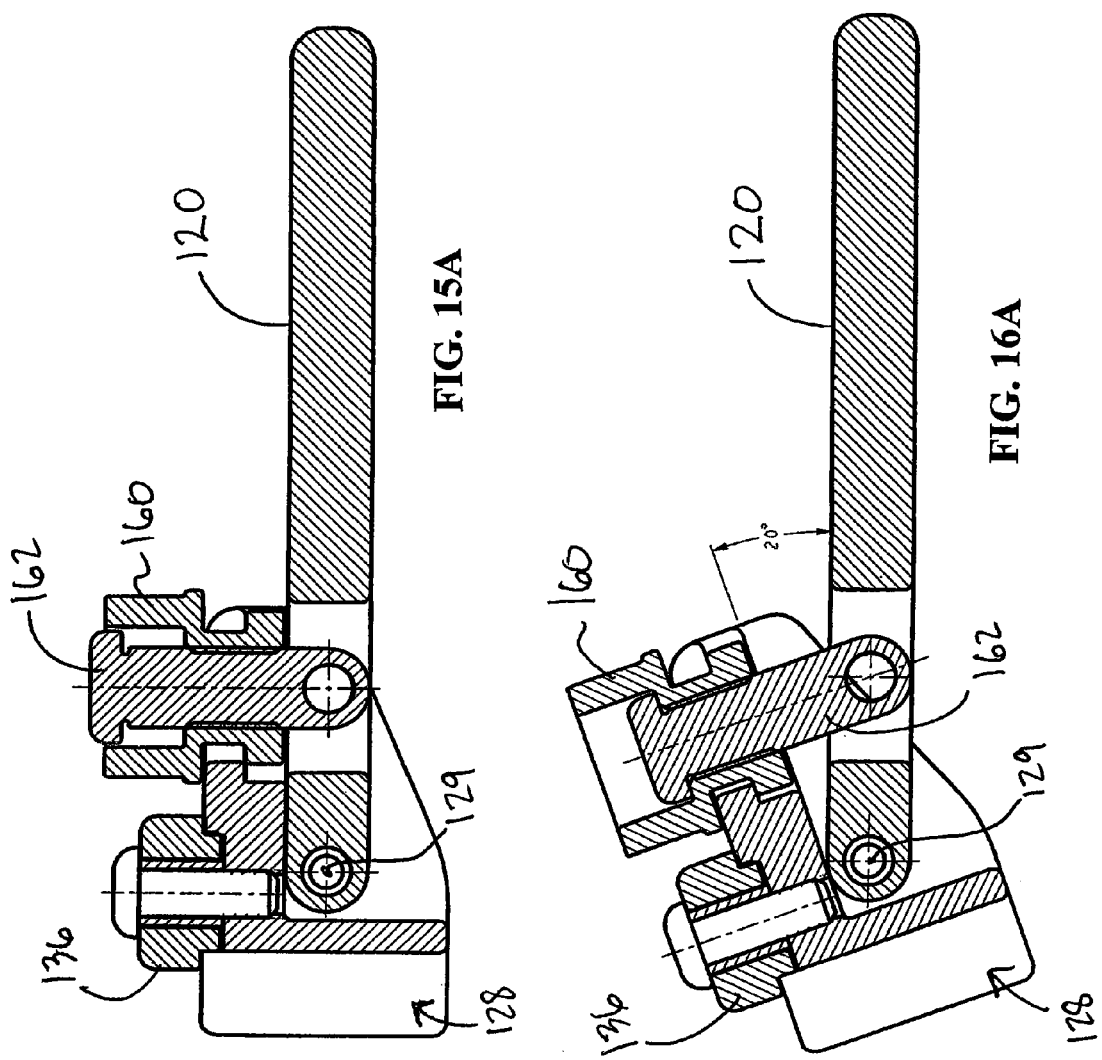
FIG. 15A
FIG. 16A

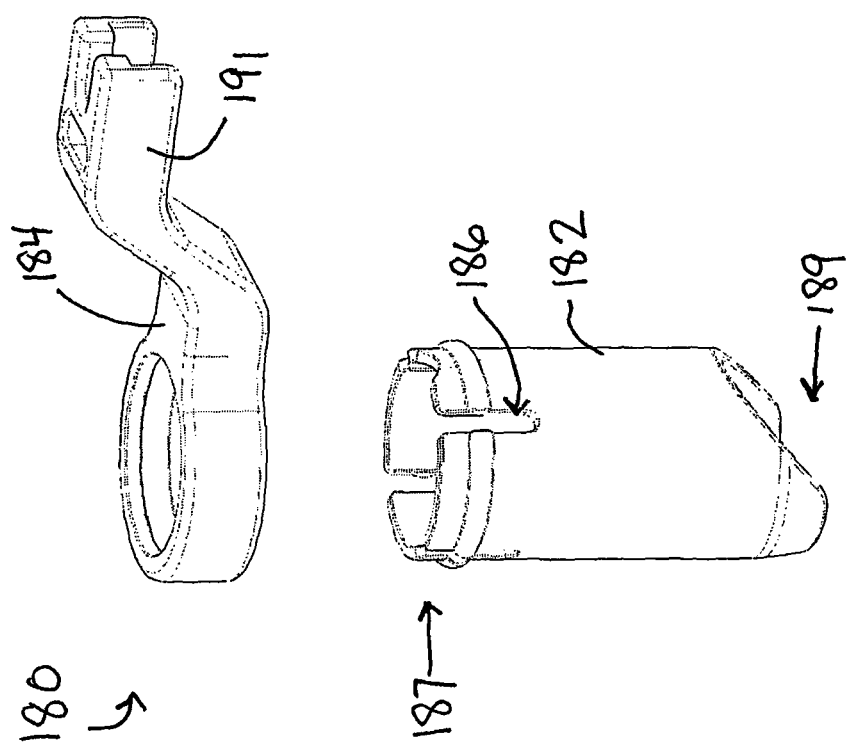

SURGICAL RETRACTOR SYSTEM

CROSS-REFERENCE TO RELATED APPLICATIONS

The present application is a continuation application of U.S. patent application Ser. No. 14/630,085, filed on Feb. 24, 2015, which is a continuation application of U.S. patent application Ser. No. 13/070,033, filed Mar. 23, 2011, which is a continuation of U.S. patent application Ser. No. 11/422,511, filed Jun. 6, 2006, now issued as U.S. Pat. No. 7,935,053, both of which are entitled "Surgical Retractor System." Each of the references cited herein is hereby incorporated by reference in their entirety.

FIELD OF THE INVENTION

The invention generally relates to devices and methods that improve surgical procedures by, for example, providing a working space for the procedure and improving the surgical conditions for the practitioner of a procedure.

BACKGROUND OF THE INVENTION

In surgical procedures generally, surgeons try to keep incisions as small as possible to minimize or reduce trauma to the patient and damage to tissue. However, it is usually necessary that the surgeon have a clear view of the operating field. Also, an opening may need to be enlarged to accommodate the passing of medical implants therethrough.

In the field of spine surgery, there is an increasing interest in developing minimally invasive methods, as opposed to conventional "open" spine surgery. The goals of these less invasive alternatives are to avoid the surgical exposure, dissection, and retraction of muscles and tissues that is necessary with "open" surgery. In general, a minimally invasive spine surgery system should be able to perform the same procedure as the traditional open technique, but through smaller incisions. As a result, some physicians feel that using a minimally invasive spine surgery system generally causes less soft tissue damage, reduces blood loss and reduces recovery time. In addition, patients generally prefer the smaller scars that are left using a minimally invasive approach.

A variety of retractors are available for use in surgical operations to reposition muscular tissue, vessels, nerves, and other tissue with the aid of retractor blades, thereby providing access to the site of the operation. Surgical retractors are particularly important in performing surgical procedures that involve the spinal column, where access to the surgical site can be obtained through a posterior, anterior, lateral, or combined approach.

Many current retractors have several shortcomings. For example, most currently available retractors are large and cumbersome, requiring a long incision length that traumatizes the patient's muscles and tissue. Also, some current retractors provide so much variability and adjustability that they are unwieldy, fiddly, and/or difficult to adjust or maneuver and are simply impractical for use in a typical surgical environment. However, other retractors may not provide sufficient adjustability. For example, some retractors do not allow independent pivoting of an individual retractor blade, while others may only provide for retraction of coupled pairs of blades as opposed to independent retraction, and still others may only allow for finite adjustment constrained to a rack and pinion system or a predefined arc for pivoting.

Therefore a need exists for a retractor system that overcomes or minimizes these and other problems.

SUMMARY OF THE INVENTION

Embodiments of the invention are generally directed toward a surgical retractor system having a frame and a plurality of arms connected thereto. In one embodiment, at least one arm is moveable relative to the frame and the relative movement is generally constrained to a direction along the longitudinal axis of the arm. At least one retractor blade is removably connected to each of the plurality of arms. In one embodiment, each blade is fixably rotatable about an axis normal to the longitudinal axis of the arm to which it is connected.

In one embodiment, the system includes at least four arms and at least one arm is fixed relative to the frame. In another embodiment, a plurality of arms are moveable relative to the frame, and wherein the relative movement of each moveable arm is constrained to a direction along the longitudinal axis of the arm, and wherein each moveable arm is independently moveable relative to the frame.

According to another embodiment, a bar clamp mechanism is connected to the frame and associated with at least one moveable arm to releasably clamp the moveable arm in a fixed position relative to the frame. In one embodiment, each moveable arm is non-threadedly connected to the frame and is actuatable by a manual retraction tool. In another embodiment, the longitudinal axes of the arms are coplanar. In another embodiment, the longitudinal axes do not rotate about frame.

According to one embodiment, the frame has a generally polygonal shape. In another embodiment, each of the moveable arms is selectably slidable with respect to the frame. According to another embodiment, the system comprises at least four retractor blades. In another embodiment, the blades comprise an elongate body having an inner face and an outer face and a longitudinal axis extending from a proximal end to a distal end, the inner face being generally concave and the outer face being generally convex. In another embodiment, a flexible sleeve at least partially surrounds the retractor blades. In an alternative embodiment, the flexible sleeve is made from a polyurethane rubber material

BRIEF DESCRIPTION OF THE DRAWINGS

The invention will be more readily understood with reference to the embodiments thereof illustrated in the attached figures, in which:

FIG. 15A is a cross-sectional view of FIG. 15 taken along line 15A;

FIG. 16A is a cross-sectional view of FIG. 16 taken along line 16A;

FIG. 17 is an enlarged sectional view of a portion of one embodiment of an arm assembly according to the invention; and FIG. 18 is an exploded view of another embodiment of a surgical retractor system according to the present invention

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The terms "first position," "second position," and "third position," as used herein, merely refer to dissimilar positions and are not meant to imply that all embodiments can only be adjusted to one, two, or three positions. In some embodiments, a retractor system may be adjustable to a finite number of positions. In other embodiments, the distance between one or more components can be increased or decreased to any desired extent, thereby allowing a retractor system to adjust to an almost infinite number of positions.

Figure 1:
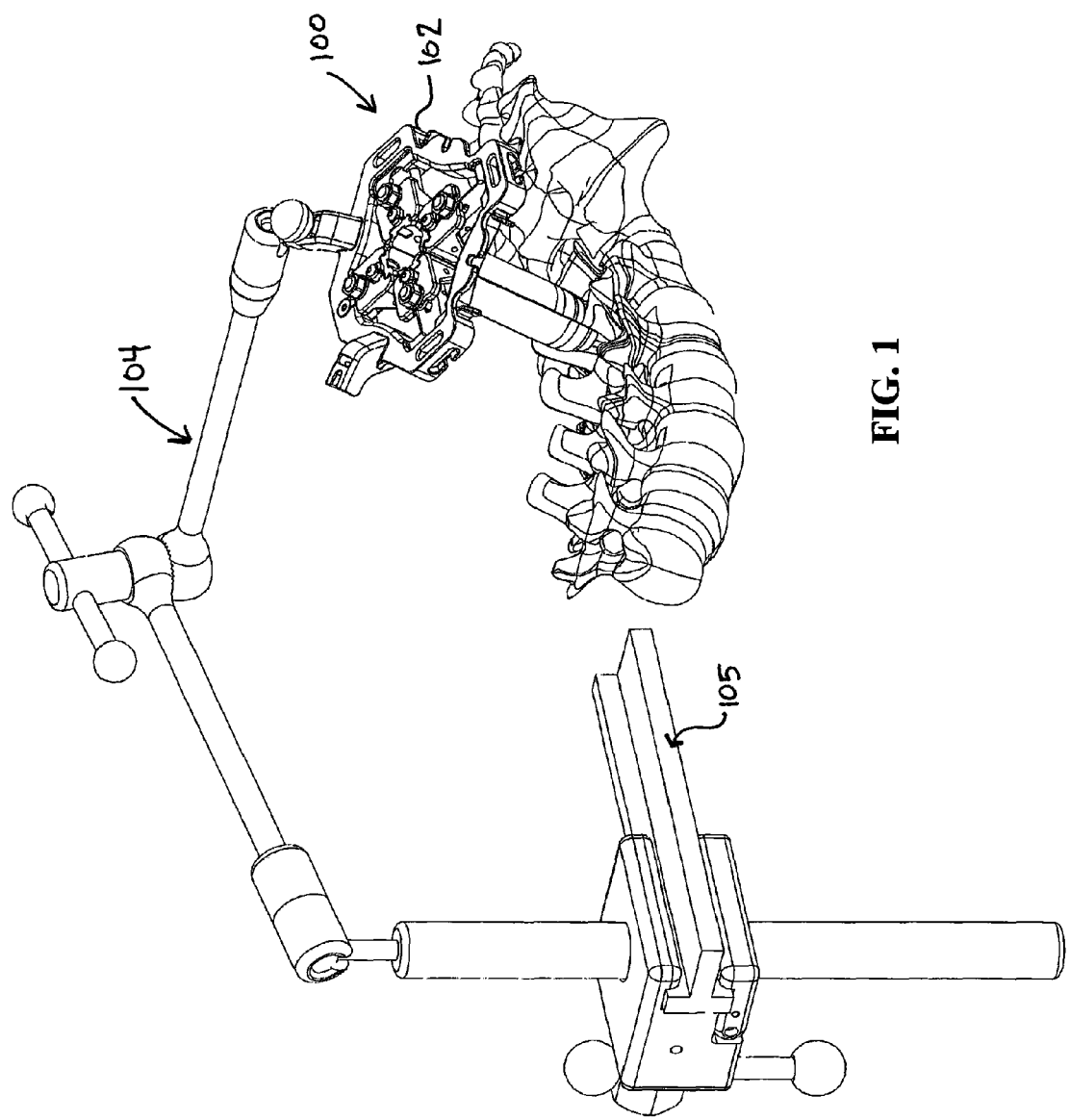
FIG. 1 is a perspective view of one embodiment of a retractor system according to the present invention positioned adjacent a bone model by a surgical arm.

Referring to FIG. 1, one embodiment of a retractor system 100 according to the invention is shown. The retractor system 100 includes a frame 102 that is attachable to an arm 104. Arm 104 may be attached to a supporting structure 105, which may comprise, for example, a table, a rack, a cart, or the like. In one embodiment, arm 104 is a surgical arm, such as a universal arm, which includes enough joints to provide a desired number of degrees of freedom to easily adjust frame 102 over an incision in a patient. The joints of arm 102 can include either a mechanism or a certain stiffness that allows the surgeon to position the surgical arm easily to a desired position and maintain the surgical arm and retractor system 100 in the new position. Utilizing and moving arm 104 allows frame 102 to be positioned in a substantially stationary position over the surgical access site. Frame 102 may provide a working support for the surgeon to rest his/her hands or arms on while performing a surgical procedure.

Figure 2:
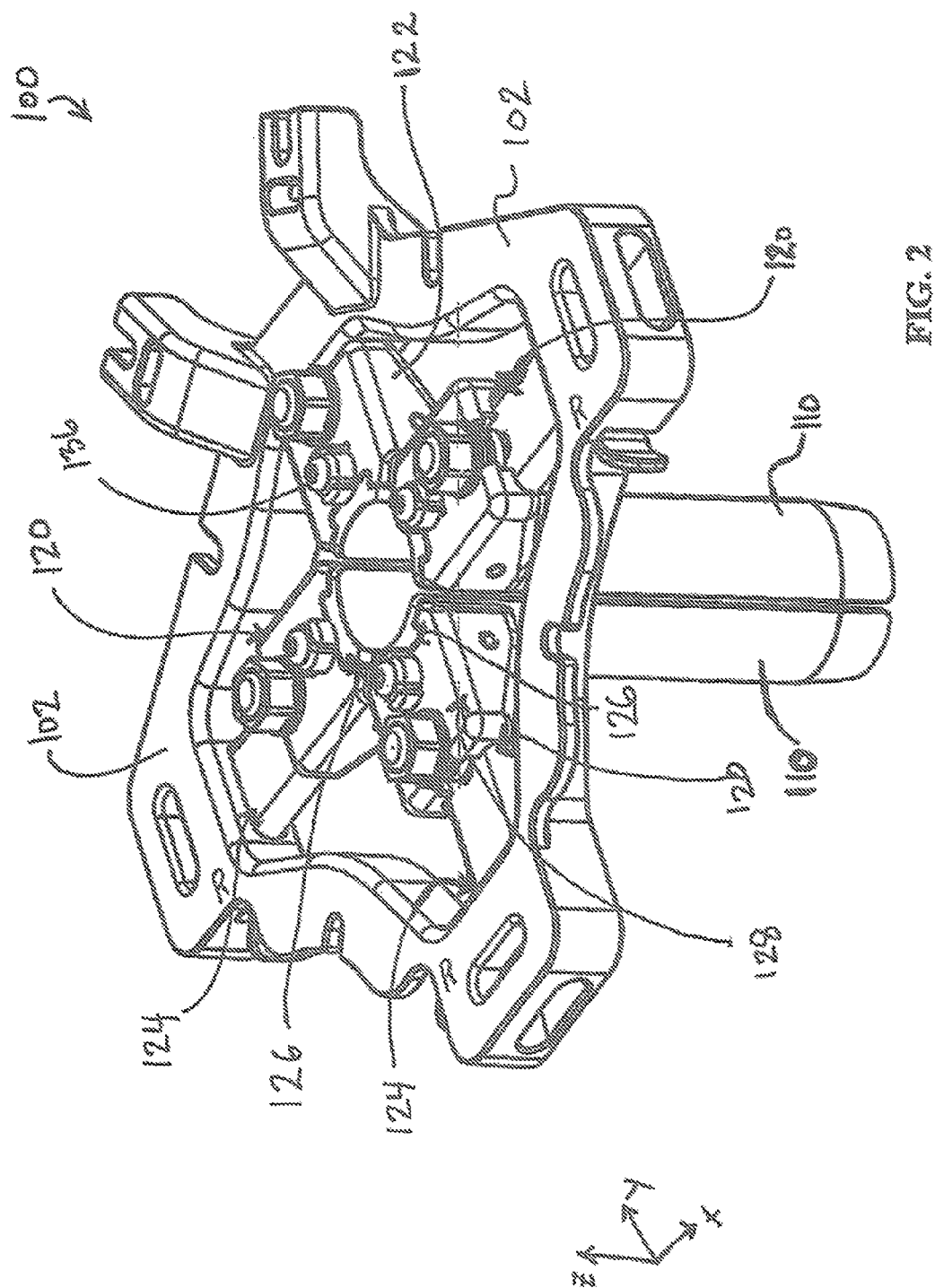
FIG. 2 is a top perspective view of one embodiment of a retractor system according to the present invention shown in a first position.
Figure 3:
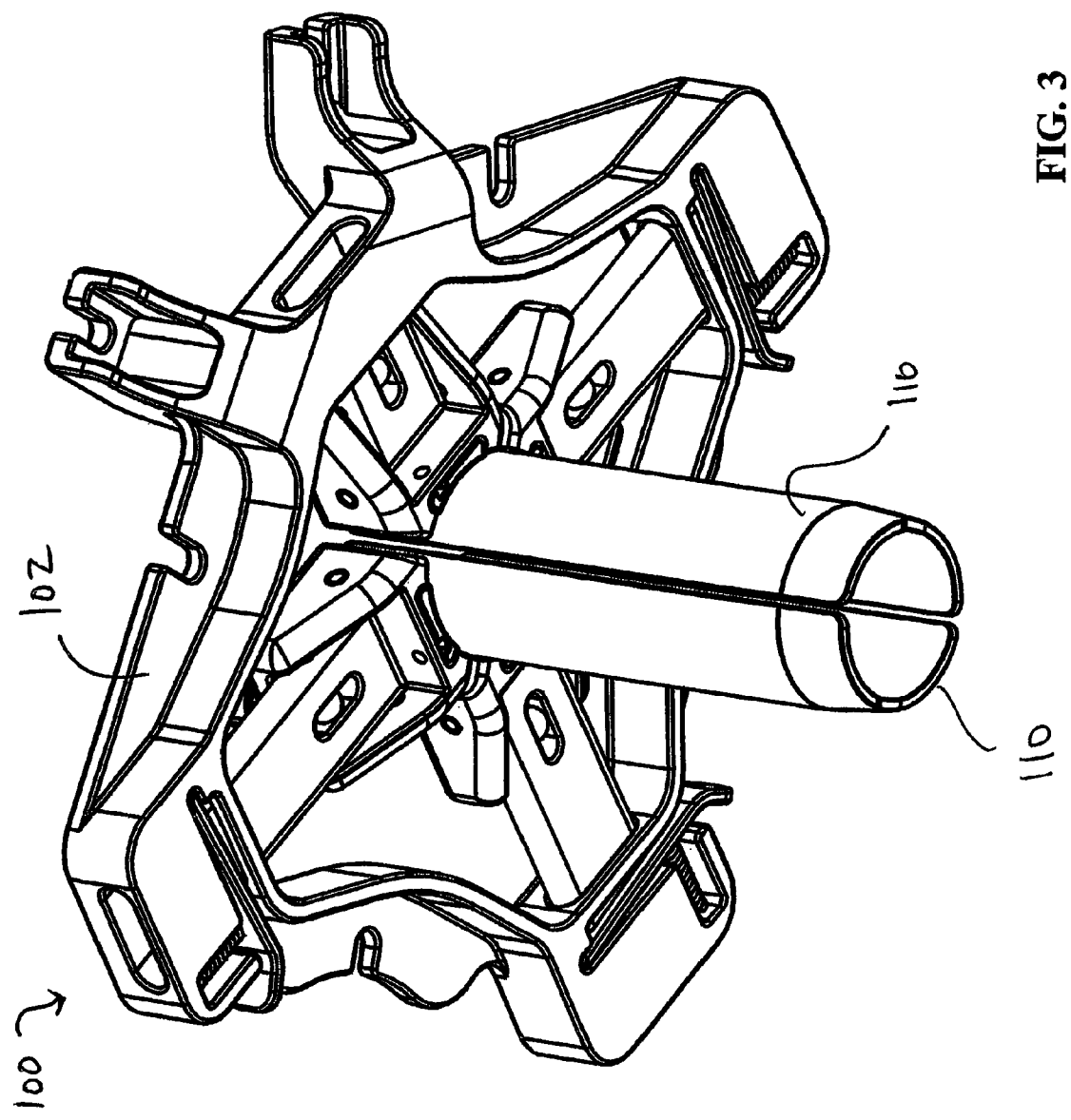
FIG. 3 is a bottom perspective view of the retractor system of FIG. 2.
Figure 4:
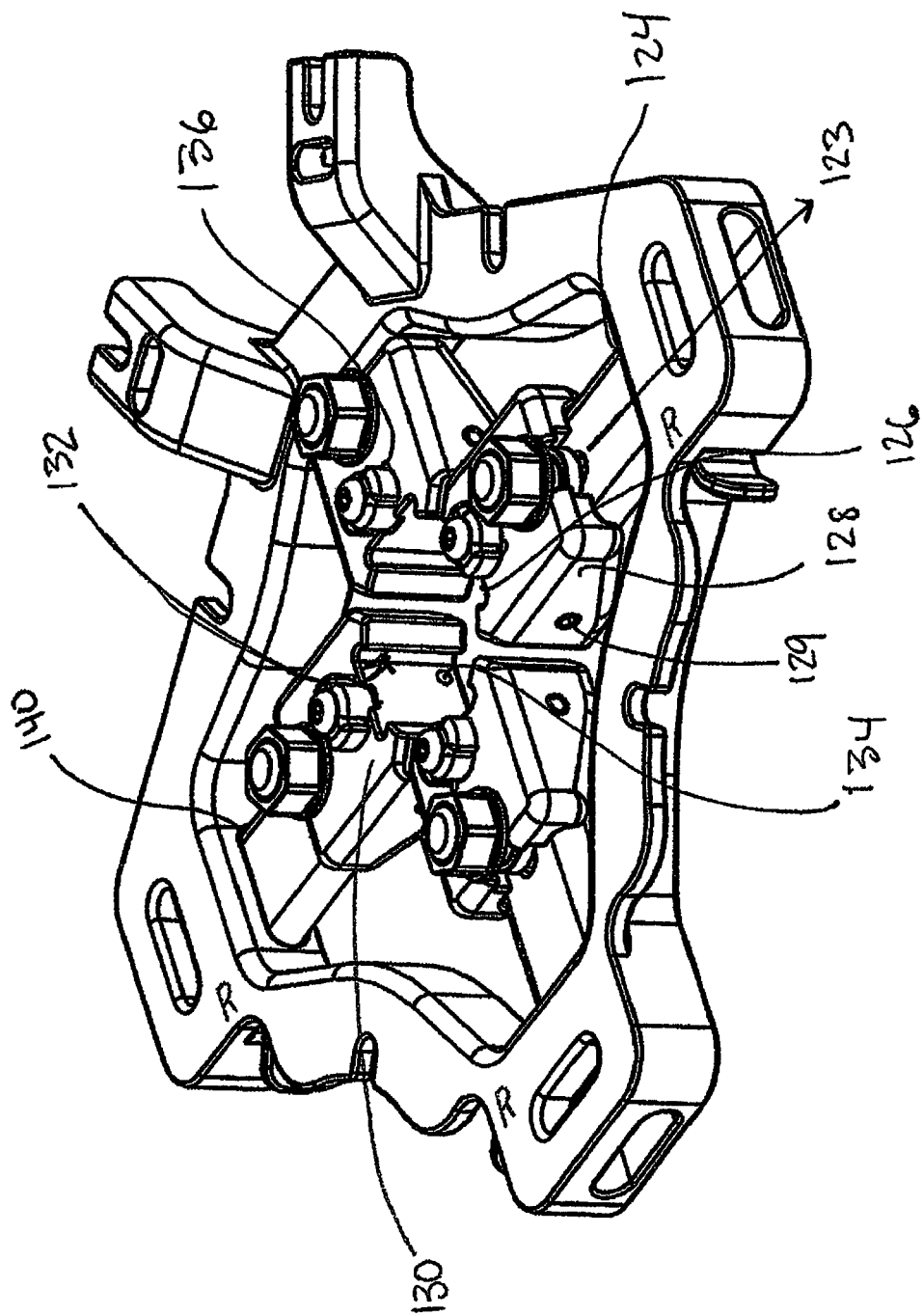
FIG. 4 is a top perspective view of another embodiment of a retractor system according to the present invention shown without retractor blades.
Figure 5:
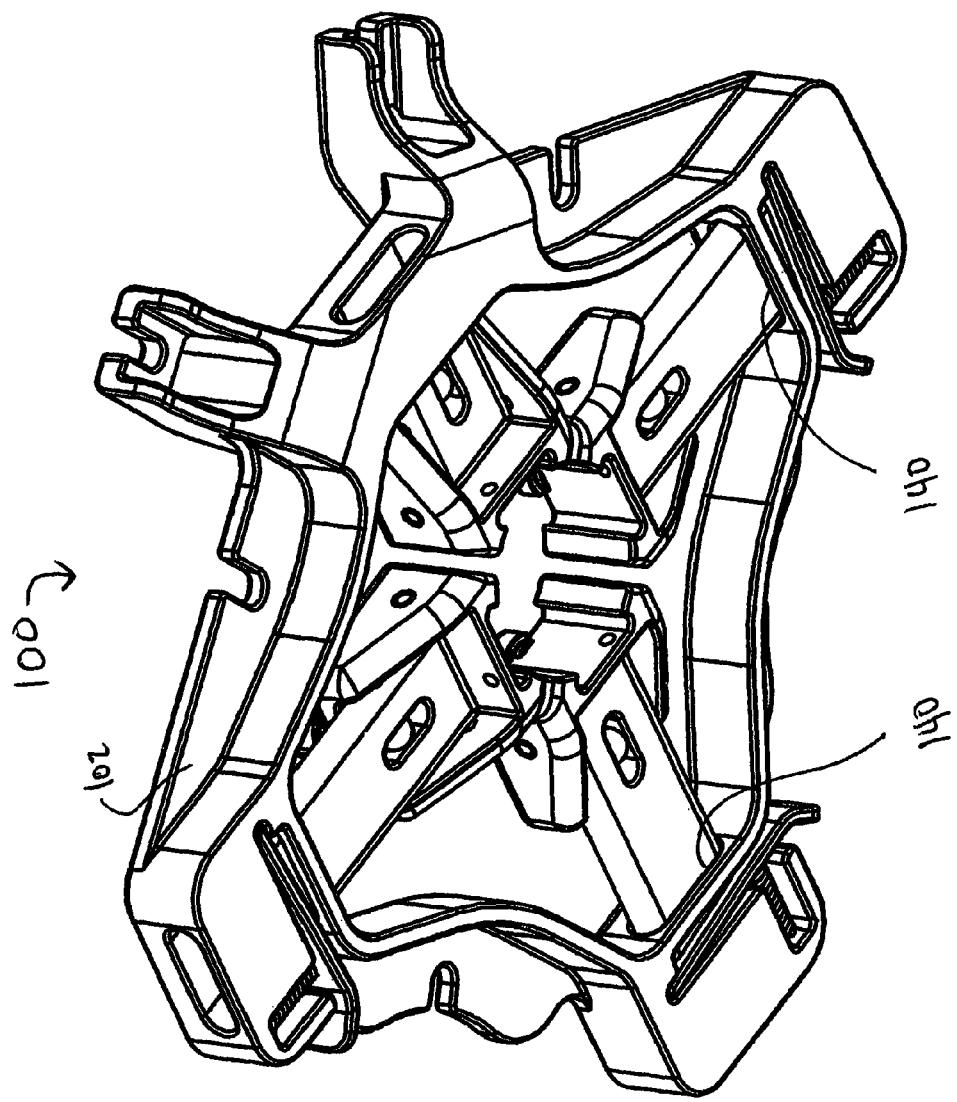
FIG. 5 is a bottom perspective view of the retractor system of FIG. 4.

As shown in FIGS. 2-3, retractor system 100 generally comprises retractor blades 110 that may be removably attached to frame 102. In one embodiment, retractor blades 110 may be attached to the inside of frame 102. Once frame 102 is positioned over an incision, such as a small minimally invasive incision, each surgical retractor blade 110 may be inserted into a body cavity through the incision. The retractor blade(s) 110 can also create or increase the size of a body cavity through insertion and/or retraction.

The retractor blade(s) 110 may be movably attached to positioning means or arms 120, 122. Each arm 120 provides the ability to independently change the position of a surgical retractor blade 110 and can be changed by a translation in an X and/or Y direction and/or a rotation about a horizontal or X-Y plane. According to one embodiment, arms 120 tightly fit within and are slideable with respect to openings 140. In operation, arms 120 may translate in a horizontal or X-Y plane when a force is applied to force the arms 120 in an outwardly direction. To hold arms 120 in a desired position, a bar clamp mechanism 142 or other fixing means, such as a screw, a latch, or the like, may be used. Such a bar clamp configuration is advantageous when compared to a threaded retraction arrangement since threads are not forced to do the retraction work and thus eliminating the possibility of cross threading. According to one embodiment, one fixed arm 122 may be provided that is fixed in the X-Y direction such that a blade 110 attached to arm 122 is not translatable in the X-Y direction, however, a blade attached thereto may still be rotatable about a horizontal or X-Y plane.

In general, each positioning arm 120, 122 extends along a longitudinal axis 123 from a proximal end 124 to a distal end 126. The distal end 126 includes a pivot member 128 to which a retractor blade 110 may be attached, whereby the pivot member is fixably rotatable about a pivot axis 129 extending transverse to the longitudinal axis 123. The term "fixably rotatable," as defined herein means that a pivot member is, alternatively, fixed or rotatable, about a pivot axis. The foregoing configuration provides flexibility in manipulating the operating field in the patient.

The pivot members 128 of arms 120, 122 may include attachment means 130 that may be used to attach retractor blade 110 to system 100. The attachment means 130 can be any type of means that enables attachment, such as a screw, pin, magnet or the like. Other examples of suitable connectors include clips, hinges, rivets, adhesives, tressits, or the like. In further embodiments, a retractor blade may be attached to, and/or extend from, a frame component. In one embodiment, the attachment means 130 comprises a dovetail groove 132 which facilitates connection and disconnection of the retractor blade 110 to and from the frame, respectively. In one variation, the dovetail groove 132 is open at the top to facilitate top loading of blades 110 and comprises a pin 134 protruding outward from the surface of groove 132 to locate and or stop the blade 110 in the vertical or Z direction. Various lengths and shapes of blades may be provided to accommodate surgical procedures at various depths subcutaneously. The attachment means is secure enough to keep the surgical retractor blades 110 attached to the arms 120, 122 while the surgical retractor blades undergo force or torque during retraction. In one embodiment, a pivotable cover 136 is provided to prevent the back out of blades 110 with respect to pivot member 128. In operation, cover 136 may be pivoted in place to cover the proximal end of a blade 110 to hold it in place in the longitudinal or Z direction with respect to pivot member 128.

In one embodiment, frame 102 comprises a generally diamond shaped frame. However, in alternate embodiments the frame can take any shape, such as elliptical, polygonal, or circular, as long as it is able to provide a base for the retractor blades 110. Examples of suitable materials of construction for the various portions of the retractor systems according to the invention include metals and metal alloys (e.g., stainless steel, aluminum, titanium, nitinol, cobalt chrome, etc.) and/or plastics (e.g., carbon fiber reinforced polymer (CFRP), ultra-high molecular weight polyethylene (UHMWPE), ultem, radel, vectra, polycarbonate, etc.).

Figure 6:
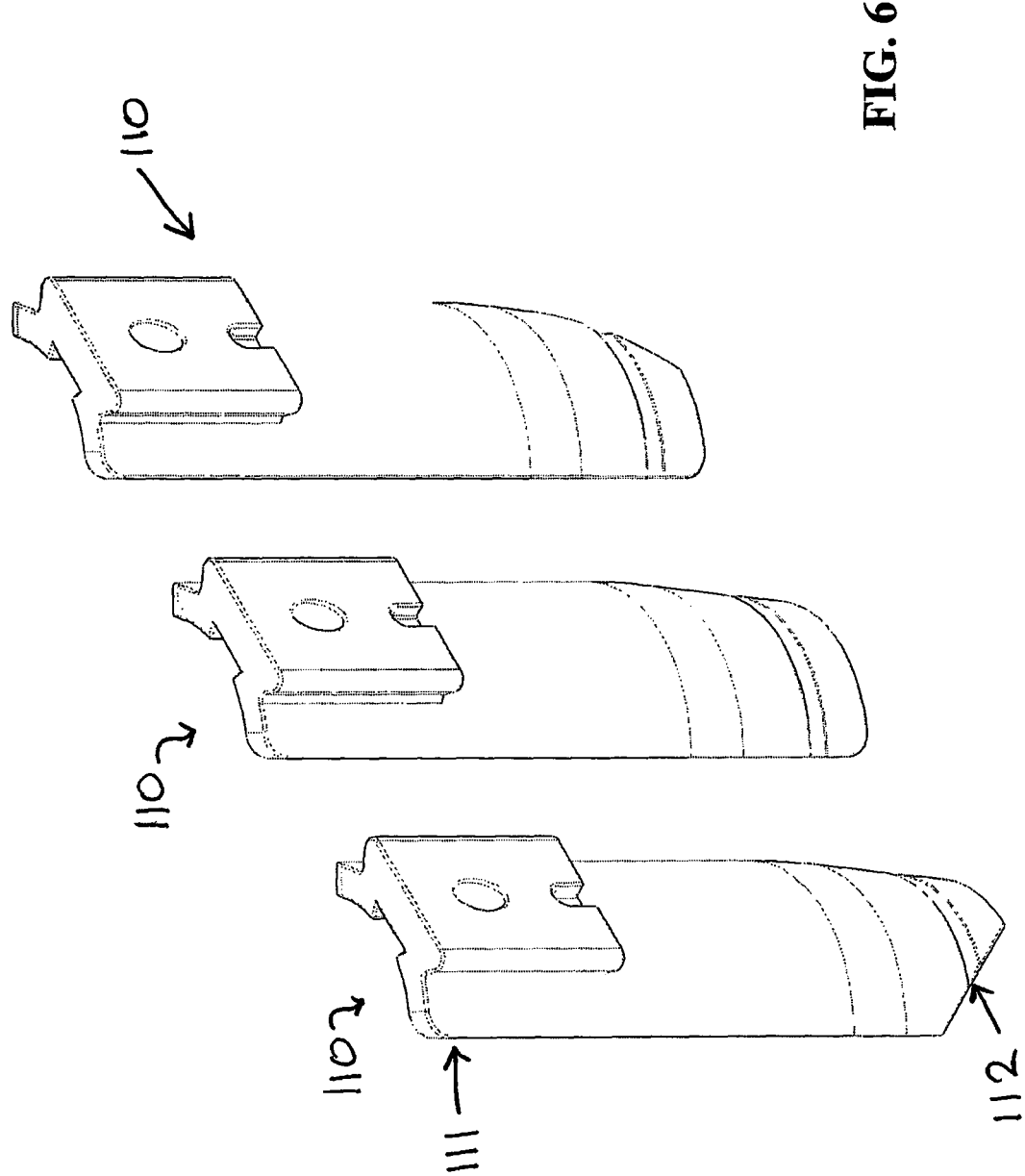
FIG. 6 is a perspective view of various embodiments of retractor blades according to the present invention.

In particular embodiments, the number of retractor blades 110 may be two or more. In one embodiment, four retractor blades 110 are provided. In general, each retractor blade has an inner face, an outer face, and a longitudinal axis running the length of the blade from a proximal end 111 to an opposite distal end 112. In one embodiment, the retractor blades 110 have a curved or partial cylindrical shape, such that when blades 110 are aligned adjacent one another, a cylinder, channel, cannula, or the like is created. The size of the retractor blades 110 is dependent on the type of surgical procedure. For delicate procedures, small or miniature blades may be used, while for macroscopic procedures, blades that are less constrained in size may be used. The retractor blades 110 may be made of any material suitable for surgical procedures known to those skilled in the art. The blades 110 can be elongated and curved. In general, any type of surgical retractor blade 110 can be used as are common in the art. Also, the type, size, and shape of surgical retractor blades 110 can be mixed together as well as changed or renewed during a surgical procedure. Referring to FIG. 6, non limiting exemplary alternative embodiments are shown, where the distal end 112 may be angled or contoured. In this regard, blades 110 may accommodate particular anatomical features as required depending on the procedure involved.

Figure 7:
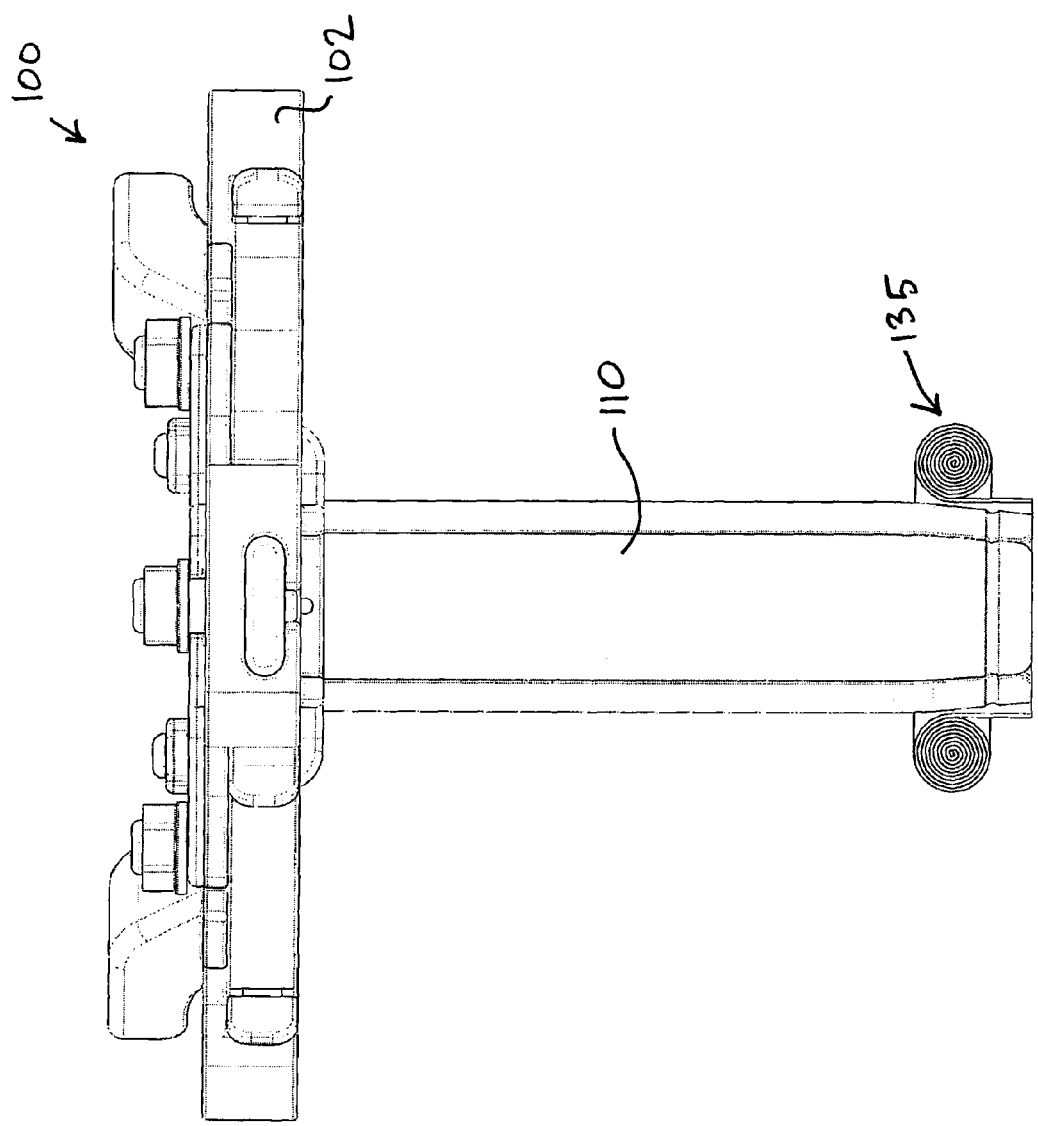
FIGS. 7-8 are partial cross-sectional views of a retractor system according to the invention showing a sleeve member assembled on the retractor blades.
Figure 8:
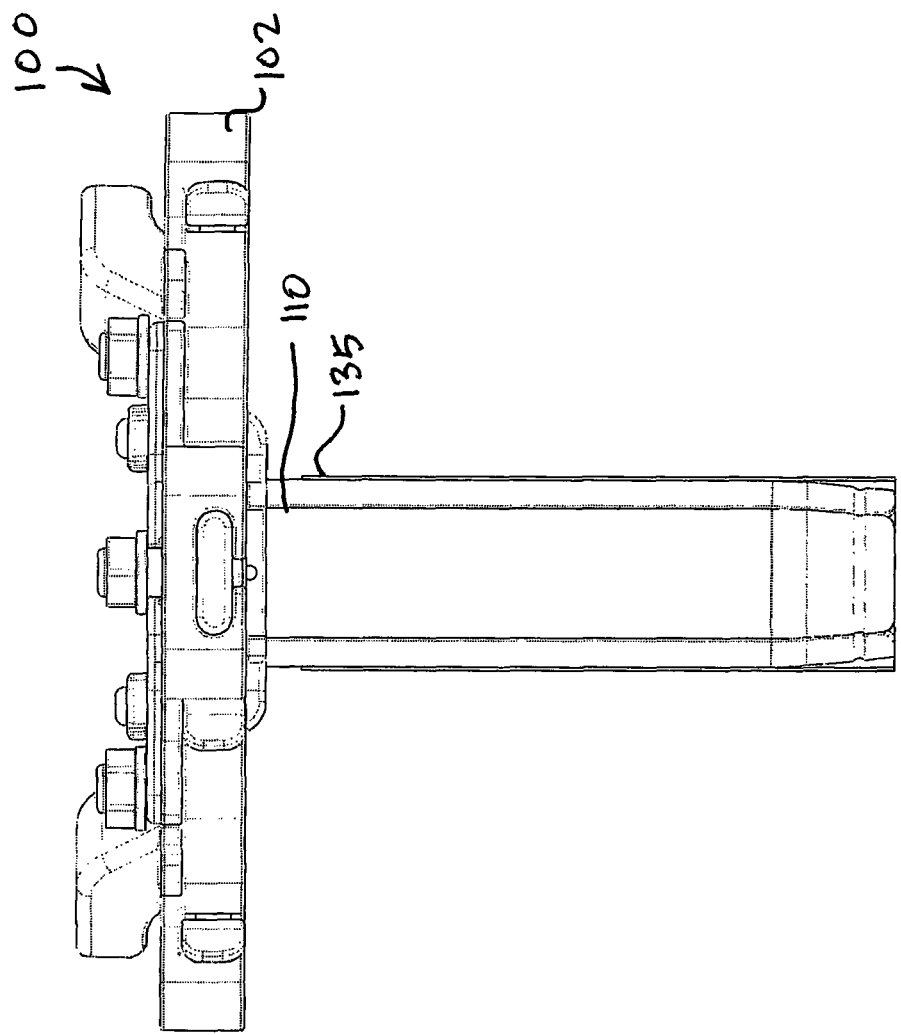

Referring to FIGS. 7-8, in one embodiment, a flexible sleeve 135 may be provided to surround the retractor blades 110 to prevent body tissue from intruding into the space created by the retractor blades once they are retracted. In general, sleeve 135 may be initially assembled on the distal end of blades 110 in a rolled-up position as shown in FIG. 7. Sleeve 135 may then be extended or unrolled in a proximal direction to surround a substantial portion of blades 110. In one embodiment, sleeve 135 may be made from a polyurethane rubber material, however, alternative appropriate materials known to those skilled in the art may also be used. In general, sleeve 135 is substantially resilient such that as blades 110 are moved and/or retracted, sleeve 135 accommodates blade movement while substantially surrounding blades 110 to prevent body tissue from intruding into the space created by the retractor blades once they are retracted. In this regard, sleeve 135 helps to provide a clean unimpeded field of vision for a surgeon utilizing retractor system 100.

The position of each retractor blade 110 can be changed independent from the other retractor blades, which allows a great amount of flexibility to the surgeon to explore an operating field. Furthermore, the position of each retractor blade 110 can be changed without changing the position of the frame 102. In other words, the frame may remain in a substantially stationary and fixed position over the incision. In this regard, a change in the operating field can be obtained by changing the position of one or more retractor blades 110.

Figure 11:
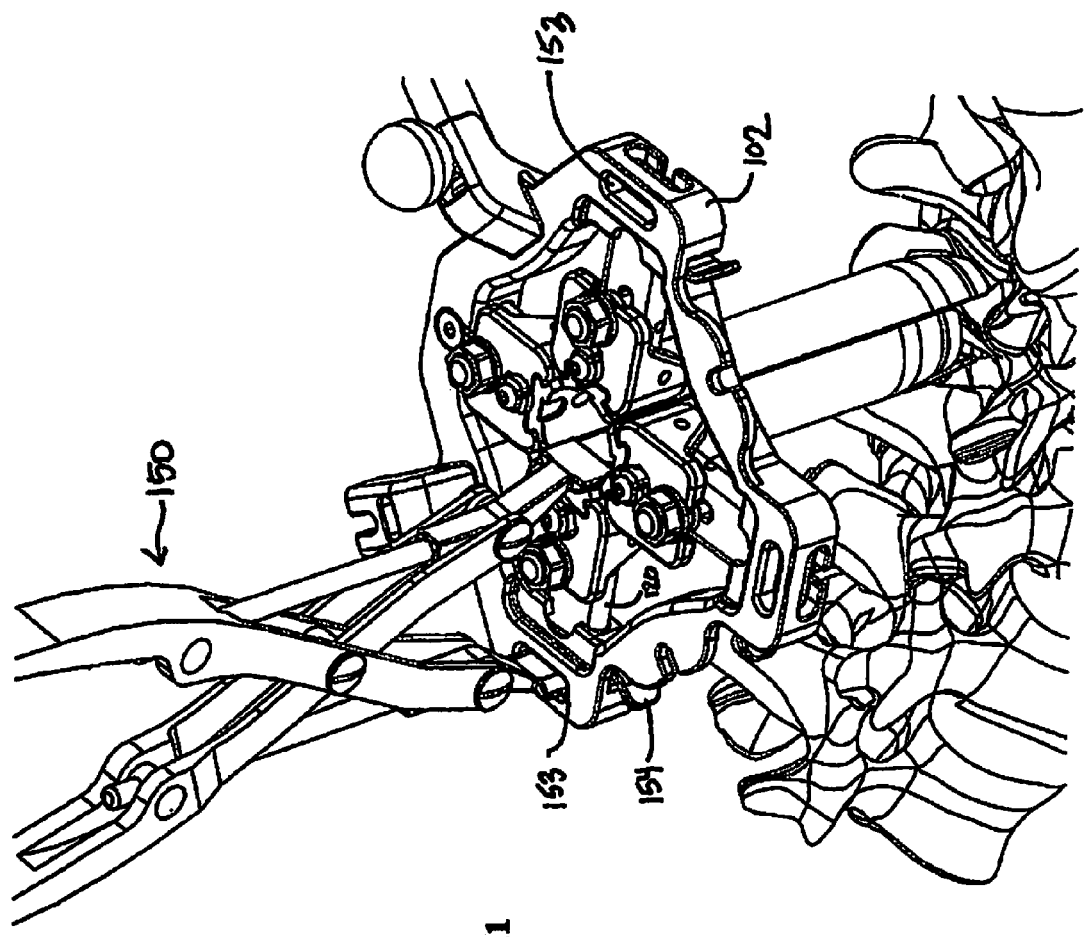
FIGS. 11-12 are perspective views of one embodiment of a retraction tool in operation with a retractor system according to the present invention.
Figure 12:
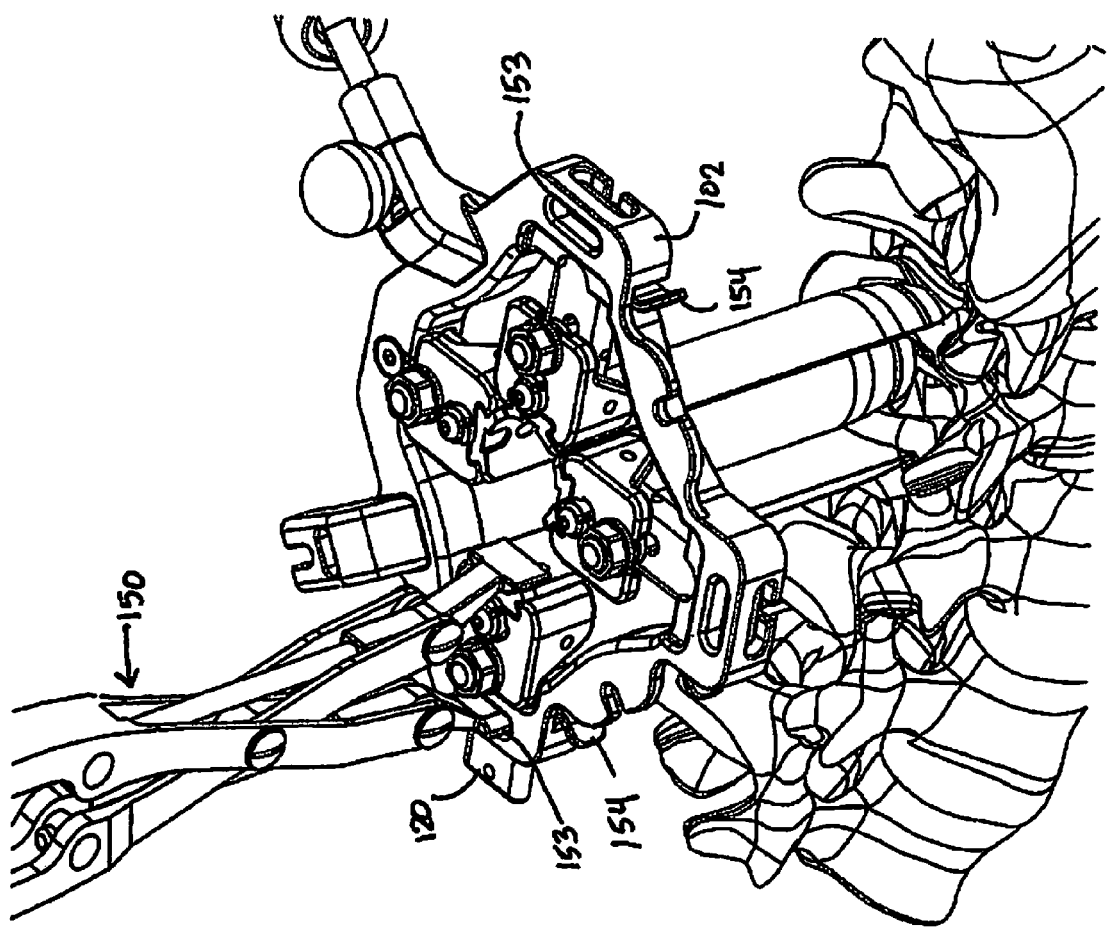

Referring to FIGS. 11-12, a handheld retraction tool 150 may be further provided to assist a surgeon in retracting, or moving in an outwardly direction, an arm 120 and, a retractor blade attached thereto. In one embodiment, best seen in FIG. 17, a spring 152 biases or pushes latch member 154 against arm 120 to prevent inadvertent inward movement of an arm once it has be retracted outward. In one embodiment, as shown in FIGS. 11-12, tool 150 may engage slot 153 in frame 102 and an inner portion of a retraction blade 110 to translate a blade 110 in an outward direction. In this regard, a surgeon may independently actuate a blade 110 while maintaining tactile feed back through the retraction tool 150.

Figures 15, 16:
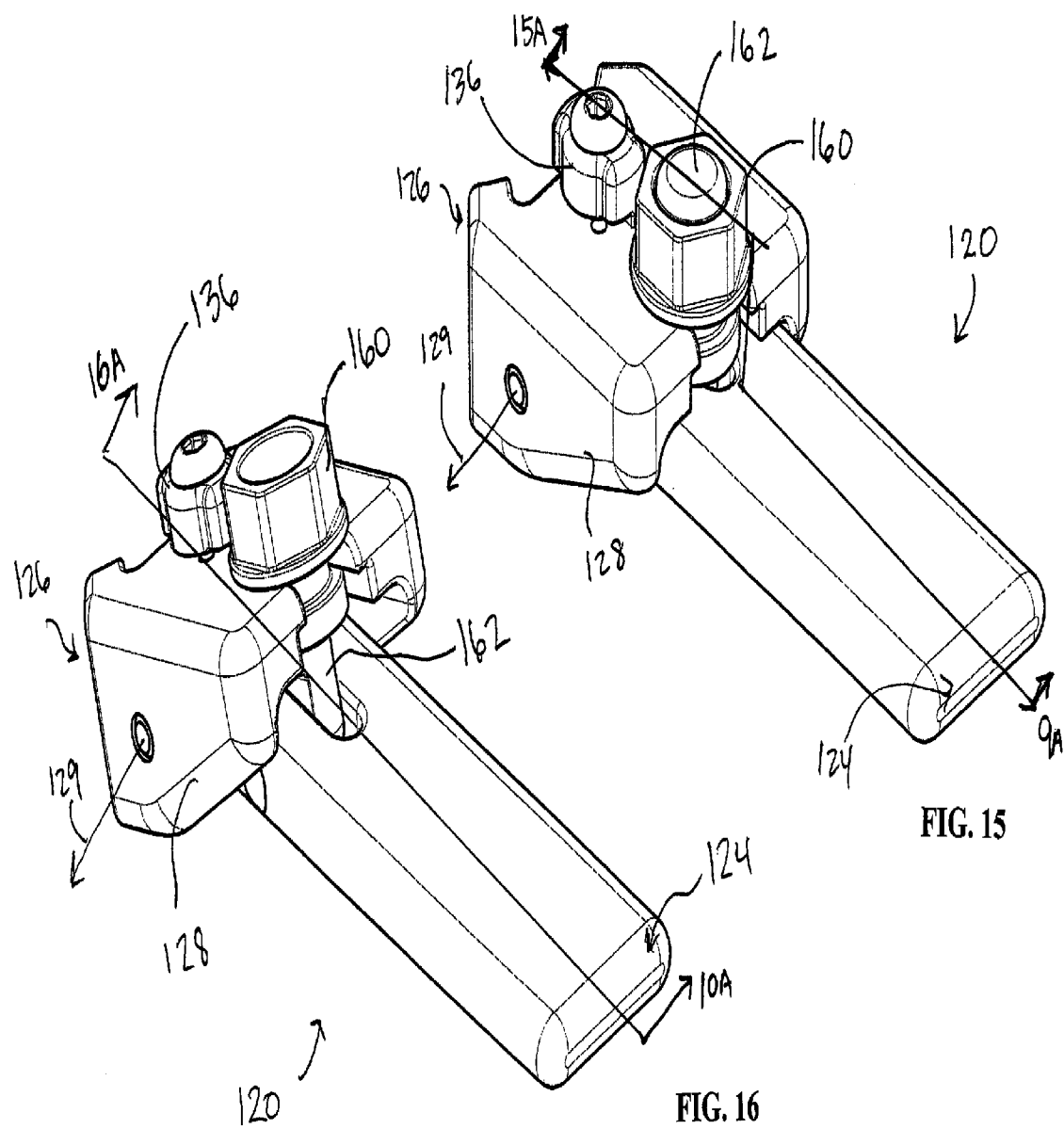
FIG. 15 is a perspective view of one embodiment of an arm assembly according to the invention shown in a first position.
FIG. 16 is a perspective view of one embodiment of an arm assembly according to the invention shown in a second position.

As explained above, in some embodiments, rotation of blades 110 about the X-Y plane can be achieved by pivoting pivot members 128 about pivot axes 129. As best seen in FIGS. 15-16, one example of a pivoting mechanism is shown. Pivoting adjustment nut 160 comprises a hollow internal portion with an internally threaded section that engages an externally threaded pivot rod 162. Rod 162 is pivotally attached to arm 120, 122 at a position spaced from pivot axis 129. Nut 160 is freely rotatable with respect to pivot member 128 yet fixed in the longitudinal or Z-direction with respect to member 128. In operation, when nut 160 is rotated a moment arm around pivot axis 129 is created, causing blade 110 to pivot with respect to arm 120, 122. Rotation of nut 160, enables a rotation about the pivot axis to establish toe-out or toe-in of retractor blade 110. As one skilled in the art will appreciate, there are different ways and techniques to establish these rotations and translations, which are all included as possible positioning means for the purpose of this invention. Therefore, these examples should be regarded as illustrative rather than limiting to the scope of the present invention.

According to one aspect of the aforementioned pivot arrangement, pivot member 128 is connected adjacent the proximal end of blade 110 and pivot member 128 is positioned adjacent the distal tip of arms 120, 122. One skilled in the art may appreciate that utilizing this configuration, the proximal end of blade 110 advantageously moves along a relatively small radius when blade 110 is pivoted which allows greater vision of the working end or distal end of the blades since a wider diameter portal or opening may be achieved at the proximal end of blades 110.

Figure 9:
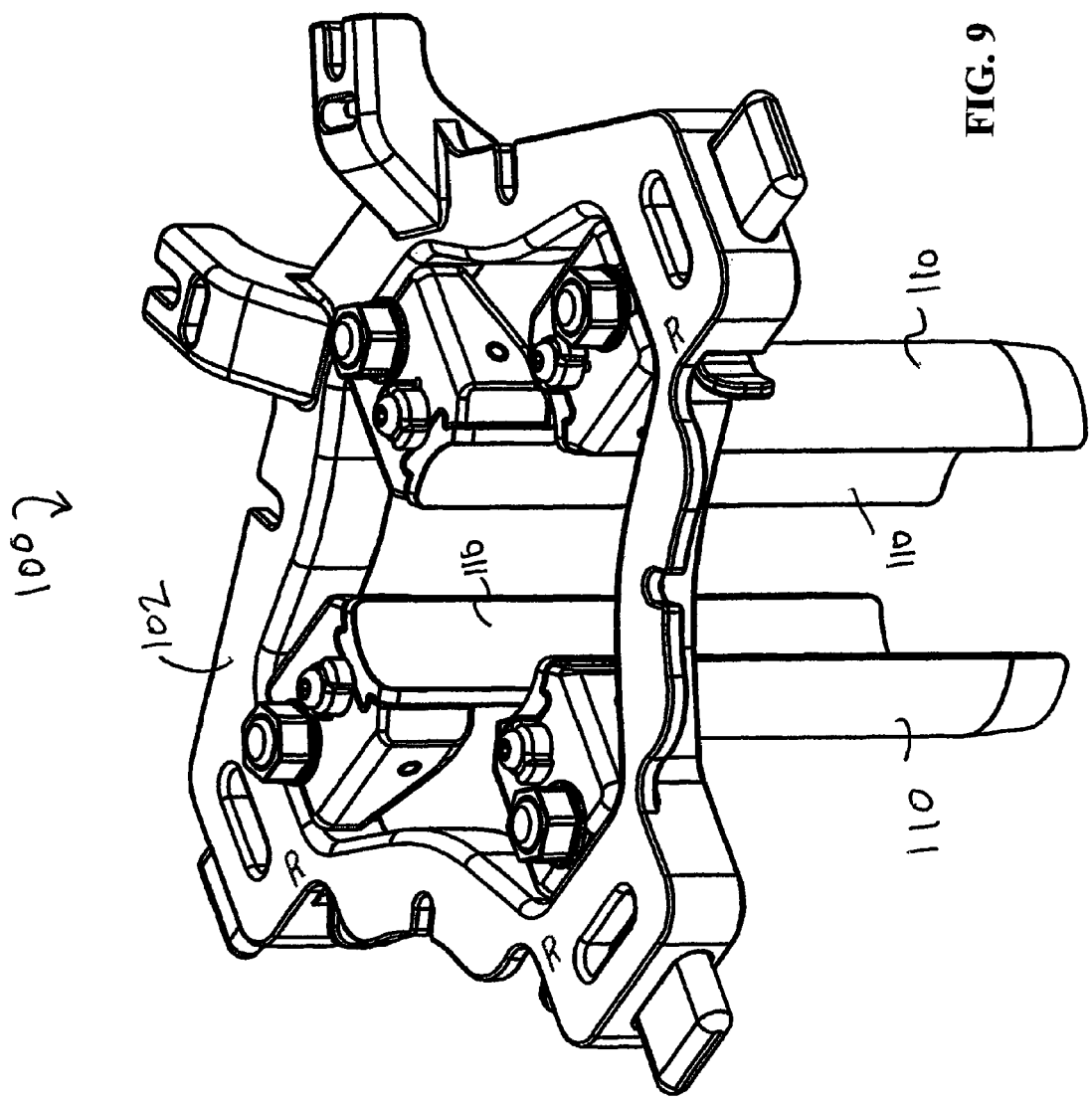
FIG. 9 is a top perspective view of one embodiment of a retractor system according to the present invention shown in a second position.
Figure 10:
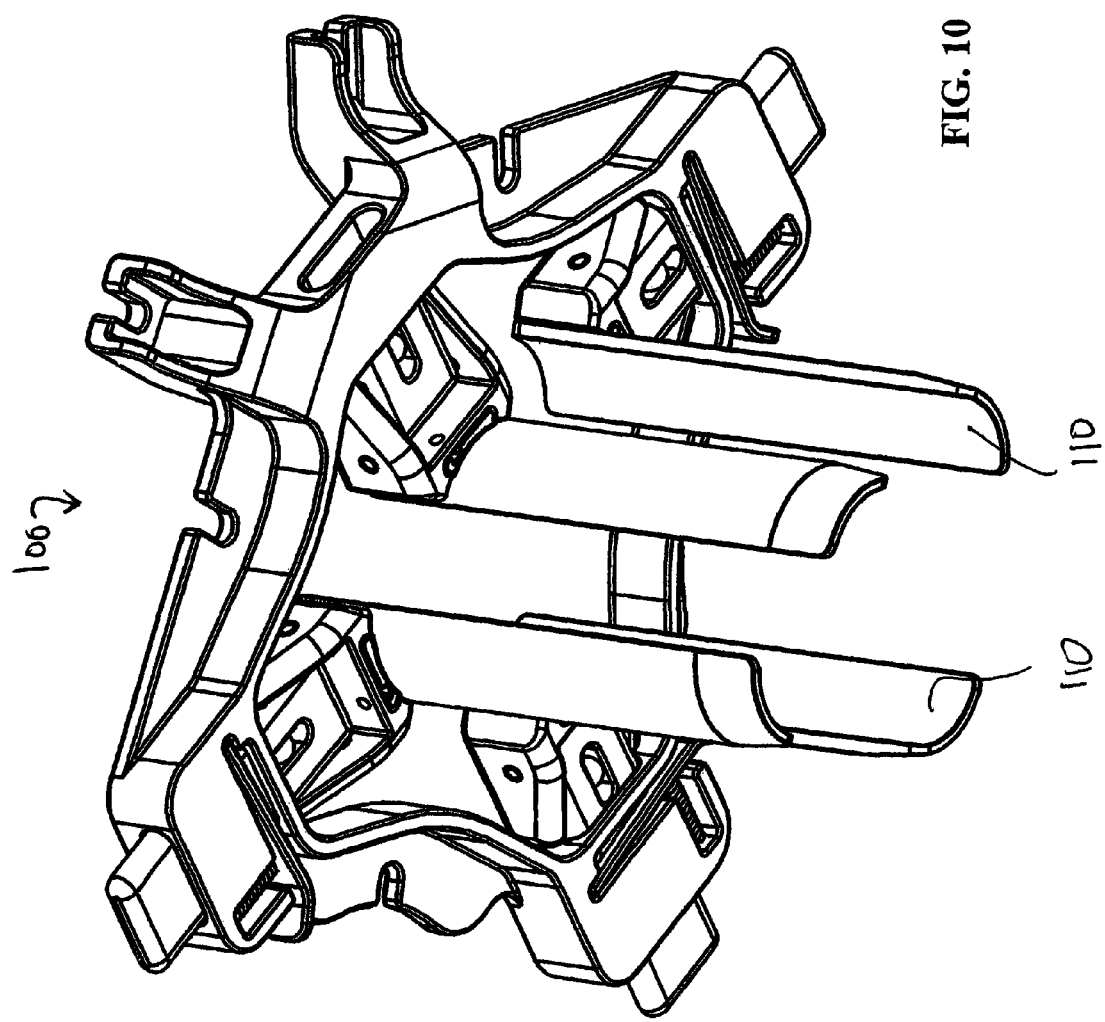
FIG. 10 is a bottom perspective view of the retractor system of FIG. 9.
Figure 13:
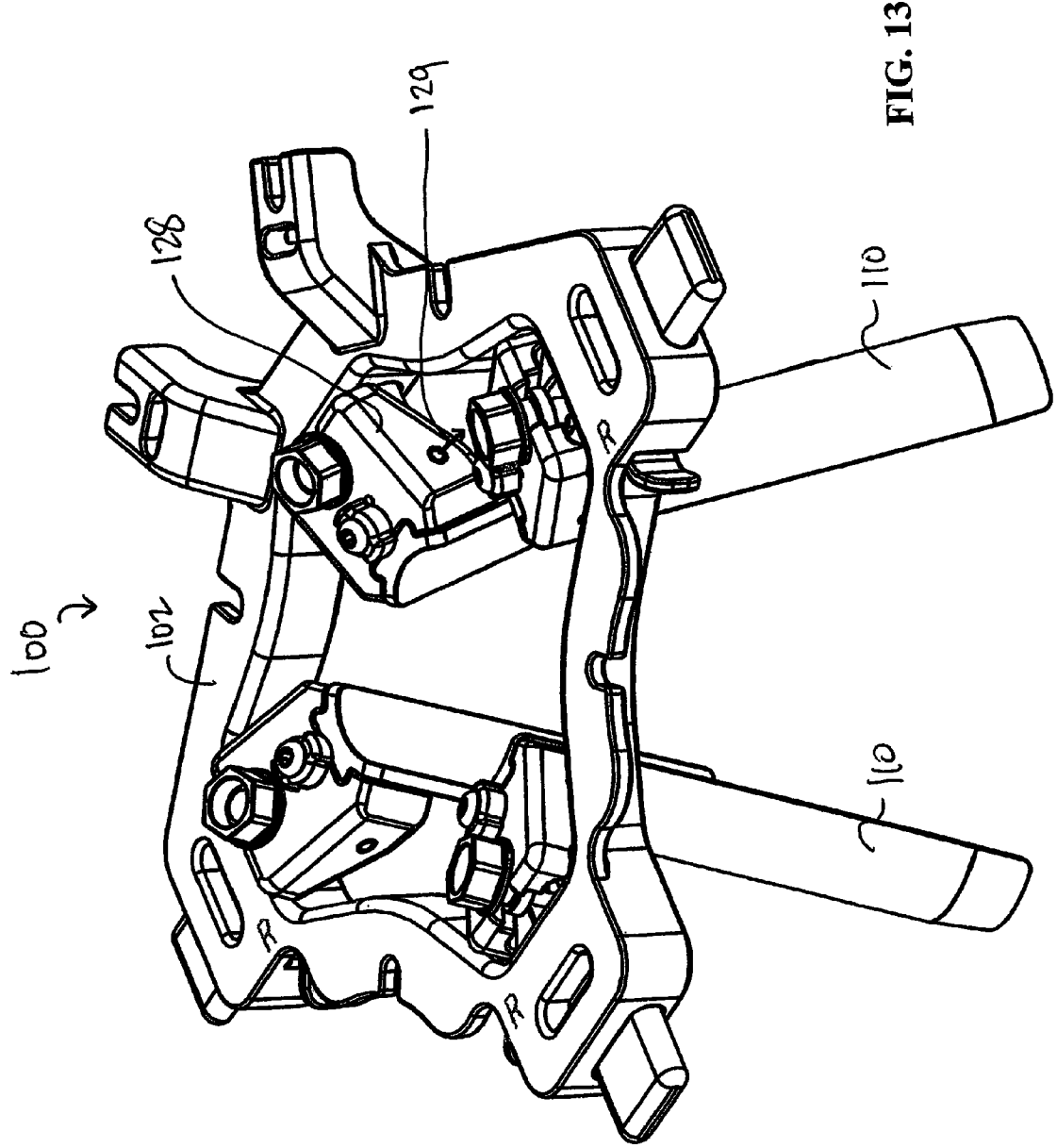
FIG. 13 is a top perspective view of one embodiment of a retractor system according to the present invention shown in a third position.
Figure 14:
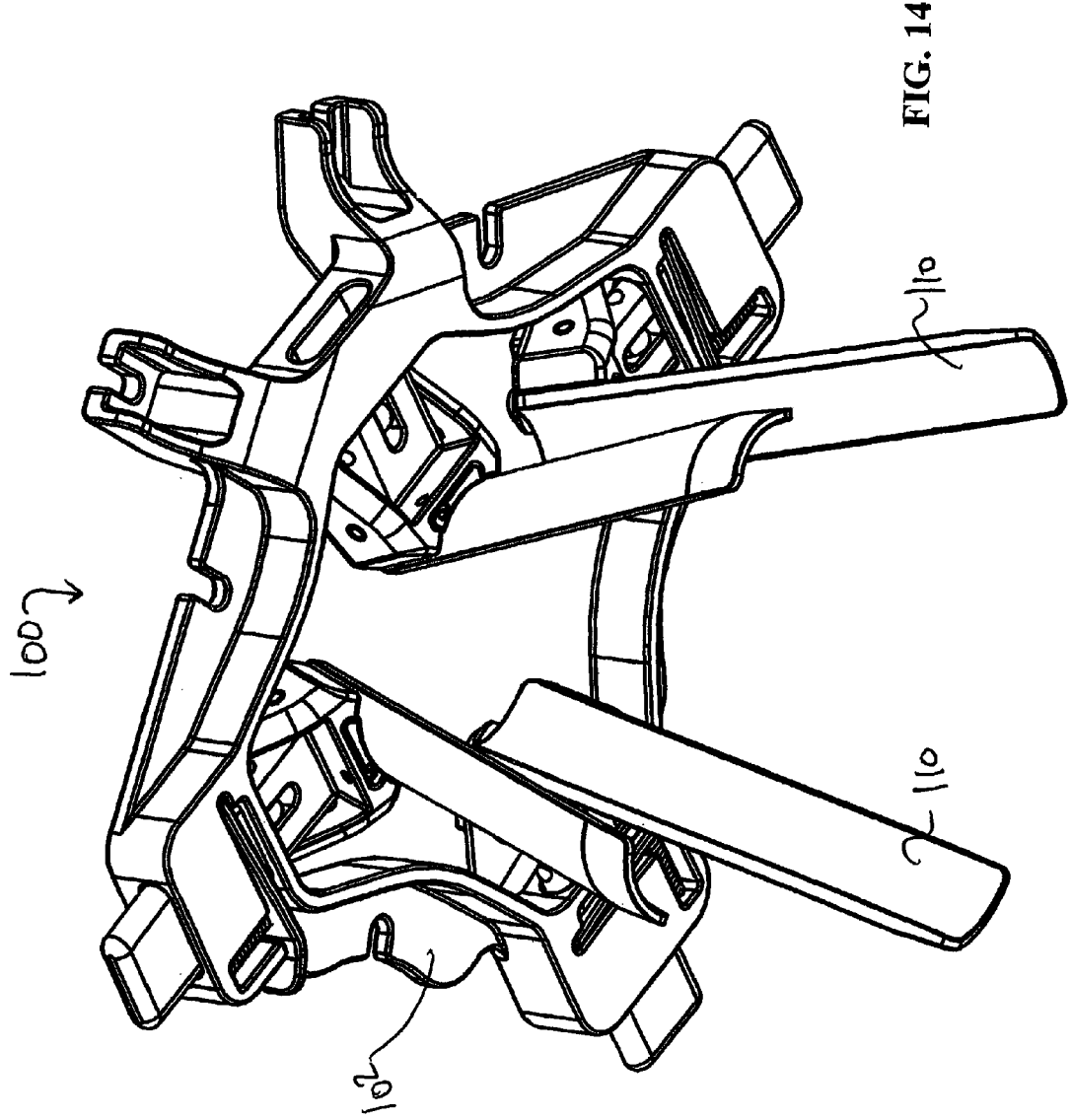
FIG. 14 is a bottom perspective view of the retractor system of FIG. 13.

Referring again to FIGS. 1-3 and 9-14, in general, the inner faces of the retractor blades define a conduit when the retractor system is at one or more positions. In some embodiments, the conduit is substantially cylindrical or substantially elliptical. Optionally, one or more retractor blades contact each other when the retractor is at one or more positions, such as for example in a first position shown in FIGS. 1-3. In still more embodiments, at least some portion of the retractor blades (e.g., the distal ends of one or more blades) provide access to a surgical site when the blades are partially or fully expanded, such as for example in a second or third position as shown in FIG. 9-10 or 13-14, respectively. FIGS. 9-10 show an embodiment of a retractor system in an exemplary second position where all four retractor blades 110 are parallel in the vertical direction and separated or retracted outward. FIGS. 13-14 show an embodiment of a retractor system in an exemplary third position where all four retractor blades 110 are positioned in a similar manner with their toes or distal ends 112 pointed outward. One skilled in the art will appreciate that there are an innumerable amount of positions that may be achieved and that the positions shown in FIGS. 1-3, 9-10, and 13-14, are merely shown for the purpose of illustration and should not be considered as limiting the scope of the invention. The number of combinations of translation(s) and/or rotation(s)

of one or more retractor blades provides extensive flexibility to the surgeon or user in exploring the desired operating field with a simultaneous effort to minimize the trauma and size of the incision.

As will be appreciated by skilled practitioners, a retractor system such as those described herein may be particularly useful for lumbar spinal surgery with either an anterior, posterior, or anterolateral approach. In one variation, the blades of the retractor system may be placed through the paraspinous muscle using a small sequential dilator without cutting any muscle or underlying fascia. The retractor system can be placed over the sequential dilator, which has created a working channel for the retractor system. Yet another example of use for the retractor relates to brain surgery and vascular surgery where access space is small or sensitive.

Some embodiments include methods of performing surgical procedures on the spine of a human using an embodiment of a retractor system of the present invention. According to one method, a patient may be positioned on a table and imaging or fluoroscopy may be utilized to target a surgical site. A lateral table rail may be provided for subsequent placement of a rigid arm assembly, such as arm 104 shown in FIG. 1.

Once a surgical site has been targeted, a longitudinal incision may be made slightly larger than the retractor system 100 of the invention when in a collapsed or closed position, as shown in FIGS. 2-3. In some embodiments, only the skin may be cut since sequential dilators may be used to pierce and dilate the fascia.

Once the incision is made, a dilator may be inserted into the incision to dilate the fascia and/or paravertebral muscle tissue down to the laminar level. Once the incision has been dilated, a retractor system 100 of the invention may be directed to the surgical site. According to some embodiments, the retractor system 100 is assembled before it is directed to the surgical site. One or more rigid arms 104 may be attached or secured to retractor system 100. Arm 104 may be secured to the surgical table and is attached to frame 102. Arm 104 can be adjusted during the surgical procedure, thereby allowing a practitioner of the invention to direct system 100 to a desired position.

Once retractor system 100 has been inserted into an incision, blades 110 can be expanded using a retraction tool, such as tool 150 illustrated in FIGS. 11-12. Each blade 110 may be retracted in the cephlad-caudal and/or the medial-lateral directions independently by inserting a part of retraction tool 150 into the slot 153 of frame 102 and another part of tool 150 adjacent the interior of a particular blade to be retracted and squeezing the handle of instrument 150 to the desired extent. As best seen in FIG. 17, the bar clamp mechanism 142 associated with each moveable arm 120 allows the arm 120 to move in one direction such that release of the handle of tool 150 instantaneously locks the arm at that position. In this regard, bar clamp 142 allows for infinite adjustment and will hold each arm 120 at the precise expanded position as desired. Blades 110 may also be independently rotated or angled about the distal end of each arm 120, 122 as desired by actuating pivot member 128 by turning nut 160. According to one embodiment of a method of the present invention a flexible sleeve may be provided to substantially surround blades 110 to prevent tissue creep or intrusion into the retracted space or surgical conduit created by the retraction of system 100.

In some embodiments, an illuminated surgical conduit may be created. In one embodiment, a light source, such as for example a thin strip light, may be provided along the interior of one or more blades 110 and may be configured to emit light towards the distal end of the blades 110. The light source may be in photonic communication with an array of fiber optic wire to power and/or control the light source. In alternate embodiments, fiber optic cable itself may be positioned along or embedded within one or more blades to emit light into the surgical conduit. In some embodiments, an optical interface may be provided adjacent the proximal end of blades 110 to facilitate modular interconnectivity of blades 110 while maintaining the integrity of the optical communication from a power source to the light source.

Referring to FIG. 18, one embodiment of a fixed diameter retractor system 180 according to the invention is shown. In general, retractor system 180 comprises a tubular member 182 that is removably coupleable to a frame member 184. According to one embodiment, tube 182 has a generally cylindrical shape with a substantially fixed diameter. In alternate embodiments, when viewed in cross-section tube 182 may have alternative shapes as desired, including but not limited to triangular, rectangular, trapezoidal, or other polygonal shapes as well as elliptical, complex curves, and figure eight shapes. As shown in FIG. 18, one or more slits 186 may be provided adjacent the proximal end 187 to accommodate slight contraction to facilitate removable connectivity to frame member 184. In this regard, according to one embodiment tube 182 may be snappably connected to frame member 184 adjacent proximal end 187. In some embodiments, tube member 182 may have a contoured or angled distal end 189 to accommodate particular anatomical features at a surgical site among other things. In particular embodiments, frame member 184 may include an extension 191 to connect to a surgical arm, such as arm 104 shown in FIG. 1. In this regard, retractor system 180 may be moved adjacent a surgical access site and subsequently positioned in a substantially stationary position over the surgical access site in much the same way as system 100, described above. Frame member 184 may provide a working support for the surgeon to rest his/her hands or arms on while performing a surgical procedure.

In some embodiments, the retractor system may include one or more features that facilitate the support of one or more surgical instruments. Non-limiting examples of surgical instruments may include a light source (e.g., a surgical light), a suction device (e.g., a suction tube), a tissue cutting and evacuation instrument (e.g., a device for cutting and removing disk material, such as a pituitary, or a device for cutting and removing bone material, such as a ronguer), or other surgical instruments known in the art.

While the invention herein disclosed has been described with reference to specific embodiments and applications thereof, numerous modifications and variations can be made thereto by those skilled in the art without departing from the scope of the invention as set forth in the claims

What is claimed is:

1. A surgical retractor system for use in surgery comprising:
   a frame comprising an upper surface and a lower surface;
   a first arm extending from the frame;
   a first retractor blade attached to the first arm extending from the frame;
   a second arm extending from the frame;
   a second retractor blade attached to the second arm extending from the frame;
   a third arm extending from the frame; and a third retractor blade attached to the third arm extending from the frame;

wherein the position of the first retractor blade, the second retractor blade and the third retractor blade can each be changed independently from each of the other retractor blades, wherein the first arm comprises a proximal end and a distal end, wherein a pivot member is received over the distal end of the first arm, wherein the pivot member includes a slot therein, wherein the first retractor blade is rotatable relative to the frame via a pivoting adjustment nut that is received in the slot of the pivot member, wherein the pivoting adjustment nut comprises a hollow internal portion with an internally threaded section that engages an externally threaded pivot rod, and wherein the pivot member comprises a dovetail groove that facilitates attachment between the first retractor blade and the frame.

2. The retractor system of claim 1, wherein the frame comprises a generally diamond shaped frame.

3. The retractor system of claim 1, wherein the first arm is slidable into an opening in the frame.

4. The retractor system of claim 1, wherein the retractor system further comprises a bar clamp mechanism received within the frame and associated with the first arm to releasably clamp the first arm in a fixed position relative to the frame.

5. The retractor system of claim 4, wherein the bar clamp mechanism comprises a latch member and a biasing member, wherein the latch member is biased in a first position to clamp the first arm in a fixed position relative to the frame and wherein the latch member is not biased in a second position to allow the first arm to move relative to the frame.

6. The retractor system of claim 1, further comprising a fourth arm and a fourth retractor blade attached to the fourth arm, wherein at least one of the first arm, second arm, third arm or fourth arm is fixed relative to the frame.

7. The retractor system of claim 6, wherein the arm that is fixed relative to the frame is fixed in translation but still rotatable relative to the frame.

8. The retractor system of claim 1, wherein rotation of pivoting adjustment nut enables a rotation of the first retractor blade via a toe-out or toe-in approach.

9. The retractor system of claim 1, wherein the retractor system is capable of being inserted via a lateral approach.

10. The retractor system of claim 1, wherein the first retractor blade is curved.

11. The retractor system of claim 1, further comprising:
a retraction tool, wherein a first part of the retraction tool is designed to be inserted in a slot in the frame, and a second part of the retraction tool is designed to be inserted adjacent the first retraction blade, wherein the retraction tool is designed to engage a bar clamp mechanism received within the frame and associated with the first arm to releasably clamp in a position relative to the frame.

12. The retractor system of claim 1, wherein the first retractor blade has a distal end that is angled with respect to a proximal end of the first retractor blade.

13. The retractor of claim 1, wherein the retractor system further comprises a flexible sleeve that is provided to surround the first retractor blade.

14. The retractor of surgery of claim 13, wherein the flexible sleeve is capable of being rolled up in a first position and unrolled into a second position.

15. The retractor system of claim 1, wherein the retractor system is capable of being placed through a paraspinous muscle using a sequential dilator.

16. The retractor of claim 15, wherein the retractor system is capable of being placed over the sequential dilator.

17. A surgical retractor system for use in surgery comprising:
a frame comprising an upper surface and a lower surface;
a first arm extending from the frame;
a first retractor blade attached to the first arm extending from the frame;
a second arm extending from the frame; and
a second retractor blade attached to the second arm extending from the frame;

wherein the position of the first retractor blade and the second retractor blade can each be changed independently from each of the other retractor blades, wherein the first arm comprises a proximal end and a distal end, wherein a pivot member is received over the distal end of the first arm, wherein the pivot member includes a slot therein, wherein the first retractor blade is rotatable relative to the frame via a pivoting adjustment nut that is received in the slot of the pivot member, wherein the pivoting adjustment nut comprises a hollow internal portion with an internally threaded section that engages an externally threaded pivot rod, and wherein the pivot member comprises a dovetail groove that facilitates attachment between the first retractor blade and the frame.

\* \* \* \* \*